United States Patent [19]

Tanaka et al.

[11] Patent Number: 4,891,163
[45] Date of Patent: Jan. 2, 1990

[54] METHOD OF PROCESSING NUCLEAR FUEL SCRAPS

[75] Inventors: Cyuzaburo Tanaka, Kitaibaraki; Teruyoshi Yazama, Katsuta; Yoshiki Miyajima, Naka; Masaharu Kashiwa, Hitachi; Hiroshi Sugai, Suginami, all of Japan

[73] Assignee: Sumitomo Metal Mining Company Limited, Tokyo, Japan

[21] Appl. No.: 914,445

[22] Filed: Oct. 1, 1986

[30] Foreign Application Priority Data

Aug. 29, 1986 [JP] Japan ................................ 61-204572

[51] Int. Cl.$^4$ ............................................. G21C 19/46
[52] U.S. Cl. ...................................... 252/627; 423/10
[58] Field of Search ...................... 252/627; 423/2, 10, 423/18, 20, 21.1

[56] References Cited

U.S. PATENT DOCUMENTS 3,959,435 5/1976 Mills et al. .
4,162,230 7/1979 Horwitz et al. .
4,461,748 7/1984 Sabot et al. .
4,574,072 3/1986 Horwitz et al. .
4,595,529 6/1986 Neace .
4,656,012 4/1987 Jdid et al. .

Primary Examiner—Harold Tudor
Assistant Examiner—Richard W. Wendtland
Attorney, Agent, or Firm—Watson, Cole, Grindle & Watson

[57] ABSTRACT

High-purity uranium can be effectively recovered from gadolinium-containing nuclear fuel scraps by dissolving the scraps in a mineral acid, extracting uranium from the resulting solution with a solvent, washing the organic phase with water or a dilute mineral acid, and counter-extraction with water or a dilute mineral acid. This invention also provides an efficient method of recovering high-purity gadolinium from the acidic washings coming from the above washing step and containing small amounts of radioactive elements (uranium, thorium and others) by adding an alkali, removing the precipitate thus formed, lowering the pH of filtrate to 2 or less, and adding an oxalic acid source to precipitate gadolinium oxalate.

8 Claims, No Drawings

METHOD OF PROCESSING NUCLEAR FUEL SCRAPS

BACKGROUND OF THE INVENTION

1. Technical Field

This invention relates to a method of processing nuclear fuel scraps containing gadolinium oxide. More particularly, it relates to a process for recovering uranium and gadolinium from nuclear fuel scraps.

2. Description of the Prior Art:

A recent trend in operating boiling water reactors ( BWR ) is to use highly enriched uranium oxide ( $UO_2$ ) fuel to ensure higher burnup and economic efficiency. Fuel of this kind contains several percent of gadolinium oxide ( $Gd_2O_3$ ), a substance having high neutron-absorbing capacity, in order to suppress excess reactivity in the initial stage of combustion and to ensure stable power output. Such nuclear fuel is manufactured by intimately mixing $UO_2$ powder and $Gd_2O_3$ powder and compression-molding the homogenous powder mixture into columns, followed by sintering. It is unavoidable that scraps are produced to a greater or lesser extent in the molding step. Because the conventional processing of such scraps will produce a $UO_2$ powder containing undesired amounts of gadolinium, such scraps are usually stored in unprocessed form.

SUMMARY OF THE INVENTION

Another object of this invention is to provide a method of recovering high-purity $Gd_2O_3$ from a solution containing gadolinium obtained from nuclear fuel scraps.

These objects can be achieved by a method which comprises dissolving nuclear fuel scraps containing gadolinium oxide in a mineral acid, extracting uranium from the resulting solution with a solvent, washing the organic phase with water or a dilute mineral acid, and recovering the uranium from the organic phase by counter-extraction with water or a dilute mineral acid; or by a modified method which comprises adding ammonia to the acidic washings coming from the above washing step and containing small amounts of radioactive elements ( uranium, thorium and others ) until the pH falls to 5 to 7, removing the precipitate which separates out, lowering the pH of the washings from which the precipitate has been removed to 2 or less, adding an oxalic acid source, and recovering the precipitate of gadolinium oxalate thus formed.

Thus the method of this invention makes it possible to recover high-purity uranium from $Gd_2O_3$-containing nuclear fuel scraps, providing a new technique for processing such fuel scraps which are expected to greatly expand in quantity. In addition, the method of this invention enables recovery of high-purity $Gd_2O_3$ from a solution containing gadolinium and small amounts of radioactive elements, providing a new technique that can isolate uranium and gadolinium separately from $Gd_2O_3$-containing nuclear fuel scraps.

DETAILED DESCRIPTION OF THE INVENTION

When uranium fuel scraps are treated with nitric acid, the uranium oxide contained comes into solution in the form of uranyl nitrate, $UO_2(NO_3)_2$, according to the following equation:

$$UO_2 + 4HNO_3 \rightarrow UO_2(NO_3)_2 + 2NO_2 + 2H_2O \text{ or}$$
$$3U_3O_8 + 20H_2O \rightarrow 9UO_2(NO_3)_2 + 10H_2O + 2NO$$

The uranyl nitrate thus formed can be isolated from the acidic solution by extraction with an organic solvent, such as tributyl phosphate ( TBP ). It is generally accepted that extraction of uranyl nitrate with TBP progresses according to the following equation:

$$UO_2(NO_3)_2 + 2TBP \rightarrow UO_2(NO_3)_2 \cdot 2TBP$$

In order to ensure sufficient extraction of $UO_2(NO_3)_2$ with TBP, the molar ratio of TBP to uranyl nitrate ( TBP/U ) should be 2 or higher. The higher the TBP/U molar ratio, the higher will be the uranium extraction rate. Since the extraction rates of gadolinium and other impurities will also increase at higher pH levels, the suitable TBP/U molar ratio is in the range from 2 to 3.

Even under the optimum extraction conditions as specified above, some gadolinium still gets involved in the organic phase; hence, subsequent counter-extraction with water or a dilute mineral acid without any pretreatment gives $UO_2(NO_3)_2$ containing much gadolinium. To avoid this disadvantage, the method of this invention involves a washing step ( washing the organic phase containing $UO_2(NO_3)_2 \cdot 2TBP$ with water or a dilute nitric acid ) prior to the counter-extraction step. This washing step essentially is a counter-extraction process, in which some $UO_2(NO_3)_2$ also moves into the aqueous phase. But it is possible to preferentially transfer gadolinium into the aqueous phase, thereby effectively reducing the amount of gadolinium left in the organic phase. The aqueous-phase/organic-phase volume ratio in this washing step must be 1/10 or lower. Given a fixed volume of washing water, gadolinium can be removed more efficiently if the water is used in portions than when it is employed all at once. Washing can also be effected by using a continuous extractor, such as a pulse column.

This washing step is followed by counter-extraction of $UO_2(NO_3)_2$ with water or a dilute mineral acid, which leaves an aqueous solution of uranyl nitrate containing less gadolinium. Ammonia is added to this solution to precipitate ADU, which is then calcined and reduced to give high-purity $UO_2$ powder. Powder containing less than 1 ppm of gadolinium can be obtained if the washing step is conducted with scrupulous care.

The washings obtained in the above washing step is an acidic solution containing gadolinium and small amounts of radioactive elements ( uranium, thorium and others ). Upon addition of ammonia to this solution, the uranium precipitates chiefly in the form of ammonium diuranate while thorium, iron and other impurities precipitate as hydroxides. The pH must be controlled at 5 to 7 in this neutralization step. This is because uranium, thorium and other impurities cannot be removed completely at a pH level lower than 5, and precipitation of gadolinium hydroxide tends to take place at a pH higher than 7. Sodium or potassium hydroxide may also be used in place of ammonia, which causes precipitation of sodium or potassium uranate, $Na_2O \cdot xUO_3$ or $K_2O \cdot xUO_3$. When the acidic solution contains iron and aluminum, the gadolinium tends to coprecipitate with the hydroxides of these metals. This trouble can be avoided by controlling the pH at lower levels within the region specified above.

After removal of the precipitate thus formed, the pH of the resulting impurity-free solution is lowered below 2, and gadolinium is isolated as oxalate by addition of an oxalic acid source, such an oxalic acid, ammonium oxalate and potassium oxalate. The amount of oxalic acid source to be added should preferably be 1 to 2 times as much as the theoretical quantity necessary for the formation of gadolinium oxalate.

The gadolinium oxalate thus recovered undergoes decomposition upon heating at about 800° C., yielding gadolinium oxide ($Gd_2O_3$). The oxide thus obtained contains little radioactive elements and other impurities, having a purity sufficiently high for practical use as neutron absorber to be incorporated in highly enriched uranium fuel.

Since $UF_6$ is used as material in the uranium reconversion step, the gadolinium-containing solution is sometimes contaminated with fluorine. When this happens, treatment of the solution with an anion exchange resin or a chelate ion-exchange resin is advisable for removal of fluorine. The use of a chelate ion-exchange resin is particularly advantageous to give high-purity $Gd_2O_3$ because radioactive elements, such as uranium and thorium, can also be effectively removed together with fluorine.

The foregoing explanation assumes the use of nitric acid for dissolution of fuel scraps, but the methods of this invention can be practiced in the same manner when any other mineral acid is used. Use of a salting out reagent, such as sodium nitrate, to enhance the rate of uranium extraction by a mineral acid, which is a known technique, may also be applied in the methods of this invention.

EXAMPLES

Example 1

$UO_2$ scraps containing $Gd_2O_3$ (3 weight % as Gd) were dissolved in nitric acid containing $NaNO_3$, giving a solution containing 192.6 g/l uranium, 27,000 ppm gadolinium, 1N nitric acid and 1N sodium nitrate. This solution was dispensed into six separating funnels, and the six fractions were extracted with TBP at TBP/uranium molar ratios of 2.0, 2.4, 2.8, 3.0, 5.0 and 10.0, respectively. The uranium concentration in the aqueous phase and the gadolinium concentration in the organic phase were found to be as shown in Table 1 (gadolinium concentrations in Examples 1 through 3 are all represented on uranium basis).

TABLE 1

| Exp. No. | TBP/U Mol Ratio | U Concn. (g/l) | Gd. Concn. (ppm) |
|---|---|---|---|
| 1 | 2.0 | 25.4 | 90 |
| 2 | 2.4 | 12.2 | 200 |
| 3 | 2.8 | 6.1 | 630 |
| 4 | 3.0 | 4.9 | 950 |
| 5 | 5.0 | 0.9 | 4000 |
| 6 | 10.0 | 0.8 | 10000 |

It is apparent from the table that the higher the TBP/U molar ratio, the higher the gadolinium concentration in the organic phase. The preferable TBP/U ratio is in the range from 2.0 to 2.5.

The organic phase obtained in Exp. No. 2 was washed with 1/20 its volume of water over a period of five minutes, the mixture was allowed to stand for 15 minutes, and the aqueous phase was withdrawn. This operation was repeated six times, and the Gd concentration in the organic phase was measured after each washing. The result is shown in Table 2.

TABLE 2

| Exp. No. | Number of Washing Cycles | Gd Concn. (ppm) |
|---|---|---|
| 7 | 1 | 55 |
| 8 | 2 | 4 |
| 9 | 3 | 0.2 |
| 10 | 4 | <0.1 |
| 11 | 5 | <0.1 |
| 12 | 6 | <0.1 |

As can be seen from the table, gadolinium can be effectively removed by washing.

The uranium contained in the washed organic phase obtained in Exp. No. 12 was extracted with water, and then converted to $UO_2$ powder by the ADU method. The concentrations of impurities in this power were: <1ppm for Gd, <0.2ppm for Ag, <5ppm for Al, <0.1ppm for B, <20ppm for C, <2ppm for Ca, <0.5ppm for Gd, <5ppm for Cl, <2ppm for Cr, <1ppm for Cu, <5ppm for F, <20ppm for Fe, <2ppm for Mo, <50ppm for N, <2ppm for Ni, <5ppm for Pb, <10ppm for Si and <1ppm for Sn.

These values are by no means inferior to those of ordinary $UO_2$ product, assuring reuse of the $UO_2$ powder obtained above without further treatment.

Example 2

An aqueous solution of uranyl nitrate obtained by dissolving uranium scraps in nitric acid and containing 120 g/l uranium, 20,000 ppm gadolinium, 1N nitric acid and 2N sodium nitrate was subjected to continuous extraction in a pulse column (300mm in diameter and about 6,000mm in height) as a uranium feed rate of 35 Kg-V/hr and a TBP/U ratio of 2.4. The organic phase was collected and subjected to continuous washing in the same pulse column as above by using 1/10 its volume of pure water. The gadolinium concentration in the organic solution fell below 1 ppm by the washing operation.

Example 3

A TBP extract containing 108 g/l uranium and 1,000 ppm gadolinium was subjected to continuous washing with pure water in a pulse column at volume ratios of 0.05 (1/20), 0.10 (1/10) and 0.15 (3/20), respectively. The result is shown in Table 3.

TABLE 3

| Volume Ratio | Concn. after Washing U(g/l) | Concn. after Washing Gd(ppm) | Gd Removal Rate* | U Recovery Rate (%) |
|---|---|---|---|---|
| 0.05 | 102 | 0.6 | $1.6 \times 10^3$ | 94 |
| 0.10 | 97 | 0.2 | $5 \times 10^3$ | 90 |
| 0.15 | 90 | 0.1 | $1 \times 10^4$ | 83 |

*(Gd concn. before washing)/(Gd concn. after washing)

As can be seen from the table, the higher the volume ratio of water to organic phase, the higher the gadolinium removal rate and the lower the uranium recovery rate. It is thus apparent that the preferable volume ratio is 0.10 or less.

Example 4

Neutralized precipitate containing 6.61 weight % of gadolinium and 0.5 weight % of uranium (2,000 g) was dissolved in nitric acid, and the insoluble matters were filtered off. The filtrate was evenly divided into five portions, ammonia was added to individual solutions to a pH of 4, 5, 6, 7 and 8, respectively, and the precipitates which separated out were filtered off. Nitric acid was added to each filtrate until the pH fell to 1, and 55.6 g of oxalic acid (Extra Pure Grade) was then added with stirring while maintaining the temperature at 50° C. The mixture was stirred at that temperature for an additional three hours and then at room temperature overnight to ensure aging of gadolinum oxalate. The precipitate was collected, washed with 0.4 l pure water, dried at 100° C. and heated at 800° C. for three hours, giving $Gd_2O_3$. Recovery rate of $Gd_2O_3$ and its composition under each pH condition are listed in Table 4.

TABLE 4

| Exp. No. | pH | Gd Recovery Rate (wt %) | $Gd_2O_3$ Composition | | Remarks |
|---|---|---|---|---|---|
| | | | Purity (wt %) | U(ppm) | |
| 13 | 4 | 96 | 99.8 | 780 | Comp. Ex. |
| 14 | 5 | 95 | 99.8 | 23 | Example |
| 15 | 6 | 90 | 99.8 | <10 | " |
| 16 | 7 | 77 | 99.9 | <10 | " |
| 17 | 8 | 36 | 99.9 | <10 | Comp. Ex. |

As may be apparent from the table, the uranium concentration in recovered $Gd_2O_3$ is too high at pH 4, while the gadolinium recovery rate is too low at pH 8.

Example 5

Neutralized precipitate containing 5.78 weight % of gadolinium, 0.2 weight % of uranium and 0.05 weight % of fluorine (2,000 g) was dissolved in nitric acid, and the insoluble matters were filtered off. Ammonia was added to the filtrate to a pH of 6.4, the precipitate which separated out was filtered off, and nitric acid was added to the filtrate until the pH fell to 3.0. The resulting solution was passed through a column packed with 20 ml of a chelate ion-exchange resin. The treated solution was adjusted to pH 1 by addition of nitric acid, and 278 g of oxalic acid (Extra Pure Grade) was then added with stirring while maintaining the temperature at 50° C. The mixture was stirred at that temperature for three hours and then at room temperature overnight to ensure aging of gadolinum oxalate. The precipitate was collected, washed with two liters of pure water, dried at 100° C. and heated at 800° C. for three hours, giving 135 g of $Gd_2O_3$. The purity was 99.9%, with the concentrations of uranium and fluorine being less than 10 ppm and less than 40 ppm, respectively.

What is claimed is:

1. A method of processing nuclear fuel scraps which contain gadolinium oxide, said method comprising the following steps: (1) dissolving said nuclear fuel scraps containing gadolinium oxide in a mineral acid and extracting uranium from the resulting solution with an organic solvent to transfer it into an organic phase; said organic solvent consisting of tributyl phosphate (TBP) which is used in a molar ratio of TBP/U of 2 to 3; (2) washing said organic phase with water or a dilute mineral acid at an aqueous-phase/organicphase volume ratio less than 1/10; (3) repeating step (2) at least once, and (4) recovering the uranium from said organic phase by counter-extraction with water or a dilute mineral acid.

2. The method of processing nuclear fuel scraps as defined in claim 1, wherein said mineral acid is nitric acid.

3. The method of processing nuclear fuel scraps as defined in claim 1, wherein said TBP/U molar ration is 2 to 2.5.

4. The method of processing nuclear fuel scraps as defined in claim 1, which further comprises the following steps: (4) adding an alkali to the acidic washings coming from said washing step and containing small amounts of radioactive elements until the pH falls down to 5 to 7, and removing the precipitate which separates out; (5) lowering the pH of the washings from which said precipitate has been removed to 2 or less and adding an oxalic acid source; and (6) recovering the precipitate of gadolinium oxalate thus formed.

5. The method of processing nuclear fuel scraps as defined in claim 4, wherein said alkali used for precipitation is ammonia, sodium hydroxide or potassium hydroxide.

6. The method of processing nuclear fuel scraps as defined in claim 4, wherein said oxalic acid source is oxalic acid, ammonium oxalate or potassium oxalate.

7. The method of processing nuclear fuel scraps as defined in claim 4, wherein said oxalic acid source is added in an amount 1 to 2 times as much as the theoretical quantity necessary for the formation of gadolinium oxalate.

8. A process for recovering gadolinium from an acid solution containing gadolinium and small amounts of radioactive elements, which process comprises adding an alkali to said acidic solution containing gadolinium and small amounts of radioactive elements until the pH falls to between 5 and 7; removing the precipitate which separates out; lowering the pH of the solution from which said precipitate has been removed to 2 or less by addition of an oxalic acid source; and recovering the precipitate of gadolinium oxalate thus formed.

* * * * *